United States Patent [19]
Cottone, Jr.

[11] Patent Number: 5,626,604
[45] Date of Patent: May 6, 1997

[54] HAND HELD STENT CRIMPING DEVICE

[75] Inventor: Robert J. Cottone, Jr., Fort Lauderdale, Fla.

[73] Assignee: Cordis Corporation, Miami Lakes, Fla.

[21] Appl. No.: 567,313

[22] Filed: Dec. 5, 1995

[51] Int. Cl.[6] ............................................. A61M 29/00
[52] U.S. Cl. ........................... 606/198; 606/1; 606/108; 606/192
[58] Field of Search ......................... 29/235, 234, 282, 29/283; 606/108, 192, 194, 198

[56] References Cited

U.S. PATENT DOCUMENTS

| | | |
|---|---|---|
| 1,306,354 | 6/1919 | Robbins . |
| 1,765,362 | 6/1930 | Berry . |
| 2,455,019 | 11/1948 | McNeill . |
| 2,468,946 | 5/1949 | Sherman . |
| 2,978,250 | 4/1961 | Adadjieff . |
| 3,353,395 | 11/1967 | Rauch . |
| 4,215,871 | 8/1980 | Hirsch et al. ........................ 279/48 |
| 4,341,002 | 7/1982 | Diba ................................... 29/235 |
| 4,553,545 | 11/1985 | Maass et al. ........................ 606/198 |
| 5,096,111 | 3/1992 | Ishikawa et al. .................... 29/235 |
| 5,201,901 | 4/1993 | Harada et al. ...................... 606/198 |
| 5,259,109 | 11/1993 | Fefeu et al. ........................ 29/235 |
| 5,437,083 | 8/1995 | Williams et al. .................... 29/235 |
| 5,476,505 | 12/1995 | Limon ................................. 623/1 |

Primary Examiner—Michael Buiz
Assistant Examiner—Patrick W. Rasche
Attorney, Agent, or Firm—Lockwood, Alex, Fitzgibbon & Cummings

[57] ABSTRACT

A stent loading device is provided for loading a stent on a catheter of the type used in percutaneous transluminal angioplasty (PTA) or percutaneous transluminal coronary angioplasty (PTCA) procedures. The device has an end unit for holding a stent, a collet having a plurality of radially compressible fingers fitted to said end unit, a main body having a plurality of finger-like extensions whose distal ends can be fitted into openings in said base unit, a proximal extension for receiving a cap with compressible washer therein fitted to said main body proximal extension, a rotatable sleeve with collet driver fitted about said collet and main body finger-like extensions and a guide wire embedded in end unit and longitudinally extending through said device to either terminate at the proximal end of said cap or extend a distance from the proximal end of said cap. The stent loading device serves as a stent delivery tool within which a catheter is inserted, after which the stent is crimped onto the catheter balloon. The stent loading device is disposable and well-suited for one-time use.

19 Claims, 6 Drawing Sheets

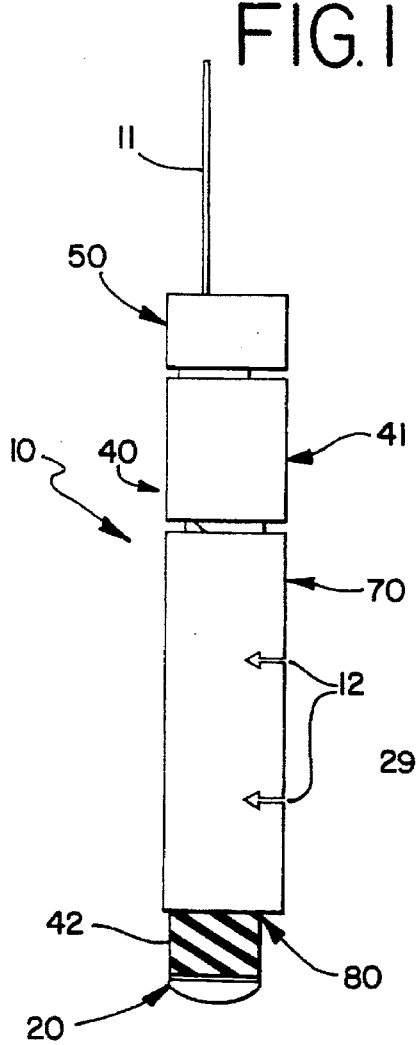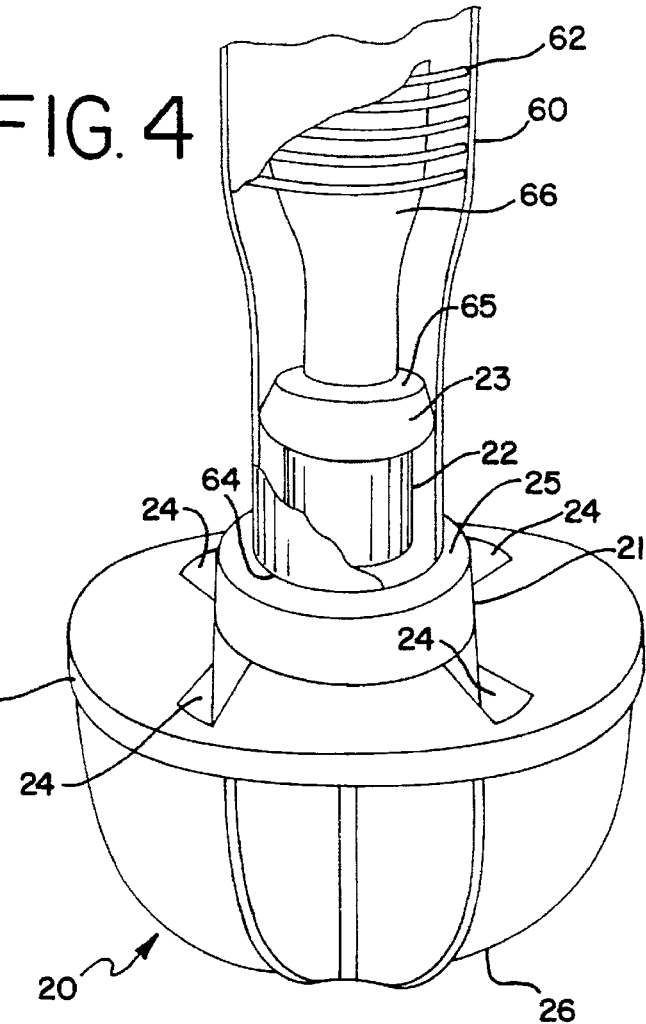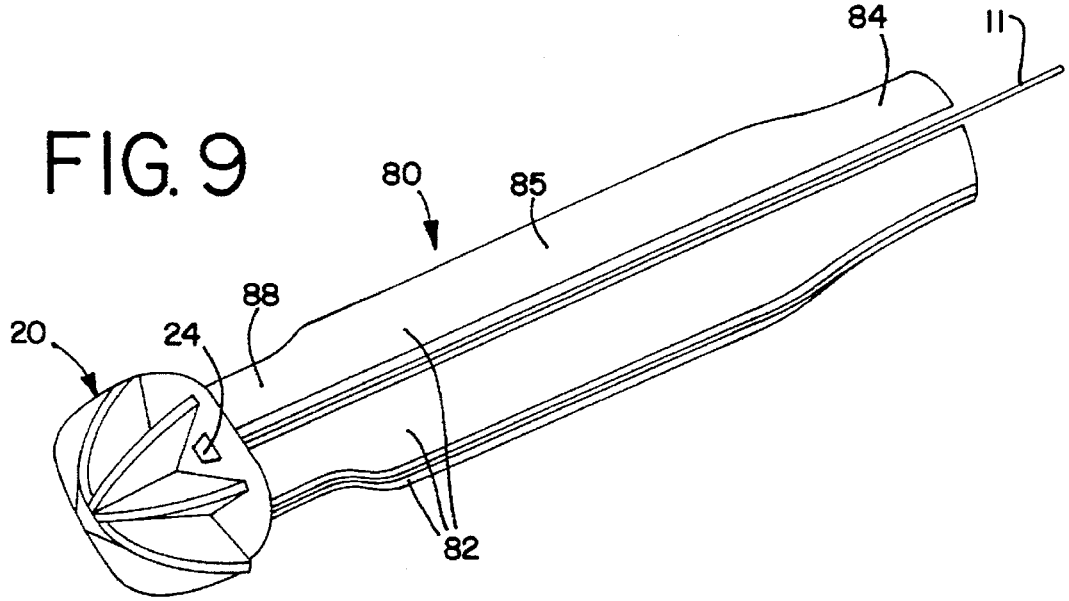

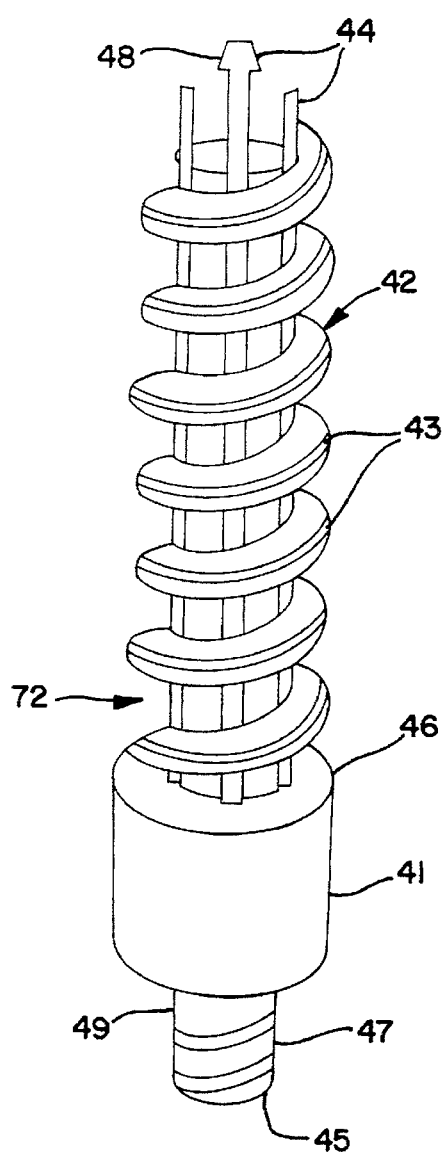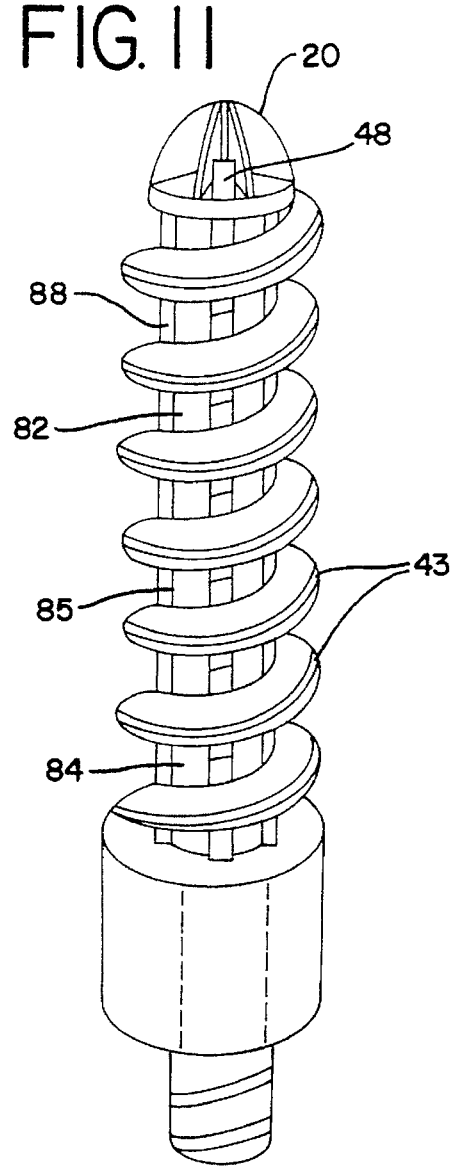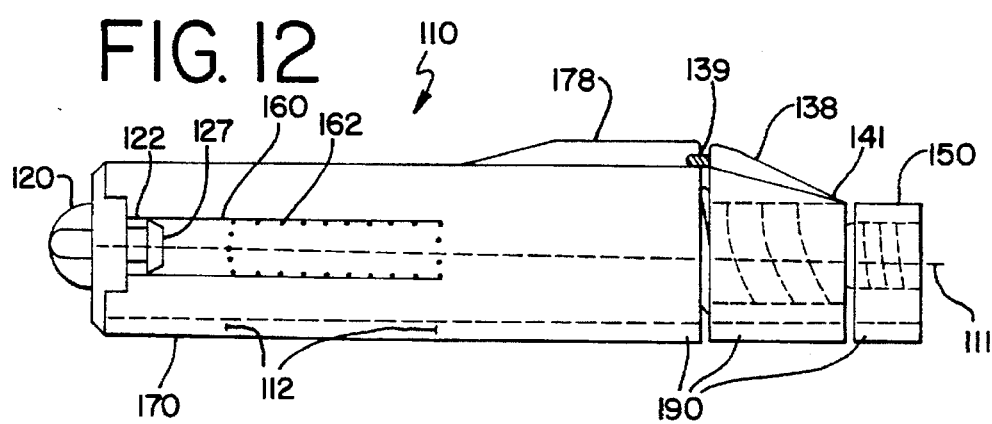

HAND HELD STENT CRIMPING DEVICE

DESCRIPTION

1. Field of the Invention

The invention relates to a stent crimping device that provides consistent and uniform stent crimping by eliminating subjective factors during the stent crimping operation. In particular, the invention is related to a hand-held stent crimping device which can be used to load a stent onto the distal end of a balloon dilation catheter assembly; for example, a catheter of the type used in percutaneous transluminal angioplasty (PTA) or percutaneous transluminal coronary angioplasty (PTCA) procedures.

2. Background of the Invention

A stent is an intravascular prosthesis that is generally introduced percutaneously, transported transluminally and positioned at a desired location within a patient. A stent is typically implanted during angioplasty in order to reduce the chance of restenosis and/or strengthen the area undergoing angioplasty or other treatment. Typically, the stent is transported to the location by a balloon catheter and is implanted by expansion of the balloon when the balloon and stent are at the desired location. Expansion of the balloon portion of the catheter can simultaneously compress plaque at that location and expand the stent to its proper implantation size. The balloon portion of the catheter is then deflated and withdrawn, leaving the stent implanted. Alternative procedures are also possible and are known to those skilled in the art. Self-expanding stents can also be used in PTA and PTCA procedures. Examples of stents useful in the PTA or PTCA procedures are described in U.S Pat. No. 4,655,771 to Wallsten, U.S. Pat. No. 4,739,762 to Palmaz and U.S. Pat. No. 5,019,090 to Pinchuk.

In practicing PTA and PTCA, stents of various diameters and lengths are used from procedure to procedure, the diameter and length of the stent being selected to correspond to the dimensions of the location undergoing repair or treatment. Delivering the stent to the location undergoing repair or treatment requires the stent to have been secured to the balloon catheter so that it does not slide off the catheter as it is being inserted and transported to the desired location within the patient. Consequently, the stent is typically crimped, rolled or otherwise secured about a catheter, generally a balloon catheter, before being inserted into the patient. Once at the treatment location, the stent is expanded to the desired size by inflation of the balloon.

Crimped stents used in PTA or PTCA procedures may be either pre-crimped about the catheter by the supplier or may be crimped on-site in sterile field by medical personnel. If stents pre-crimped about a catheter are used, generally a large stock of stent-bearing angioplasty catheters must be maintained in order to insure that one properly sized stent/catheter unit is available when it is needed. Maintaining such an inventory can be expensive. The inventory expense can be reduced by stocking separate catheters and stents, and having the surgical personnel crimp the desired stent about a selected catheter prior to a procedure. However, the proper crimping of a stent about a balloon catheter is a technique acquired only through practice and can be affected by a variety of subjective conditions. Frequently, the stents are crimped using sterile pliers. Excessive force applied during the crimping with such pliers can damage the stent and/or the catheter. The crimping problem is worsened by the small size of the stents which are typically about 3–4 millimeters (mm) in diameter before crimping and 1–10 centimeters (cm) in length or longer. Examples of the problems encountered are non-uniform crimping, the inability to judge when a reliable and uniform crimp has been achieved, and damage to the stent or catheter during crimping.

U.S. Pat. No. 5,437,083 describes a device for placing a stent about a balloon catheter. The device has a series of plates which have substantially flat and parallel surfaces that move in a rectilinear fashion with respect to each other. A stent carrying catheter can be disposed between these surfaces to affix the stent onto the outside of the catheter by relative motion between the plates. Force indicating transducers are used in conjunction with the plates to indicate the force being applied during affixation of the stent. The U.S. Pat. No. 5,437,083 patent also describes an embodiment whereby a fluid filled bladder is used to crimp a stent about a balloon catheter. Although the U.S. Pat. No. 5,437,083 device seems useful in a commercial setting, its use in a surgical theater is believed to impose some problems, particularly with regard to maintaining sterility.

With regard to the crimping of stents onto catheters, there is a need for a simple device, preferably disposable, which would (1) eliminate subjective factors during stent crimping, (2) eliminate the handling of the stents themselves in the surgical theater and (3) solve the inventory problem. It has been found that a device which has, among other elements, a collet for radially crimping a stent in a uniform manner about a catheter and a collet compressing component which causes the collet to effect such crimping fulfills the needs stated above. Examples of collet containing devices are found in tools such a drills and screwdrivers which use interchangeable bits, and certain types of pencil holders. U.S. Pat. No. 1,306,354 to Robbins, U.S. Pat. No. 1,765,362 to Berry. U.S. Pat. No. 2,978,250 to Abadjieff, U.S. Pat. No. 2,455,019 to McNeill, U.S. Pat. No. 2,468,946 to Sherman, U.S. Pat. No. 3,353,395 to Rauch and U.S. Pat. No. 4,215,871 to Hirsch et al. provide a variety of examples. However, none of the devices described in these patents would eliminate all the subjective elements if they were used or adapted to the crimping of stents onto balloon catheters. For example, the forces they exert cannot easily be limited or controlled and consequently such devices are likely to cause damage to the stent and/or catheter.

SUMMARY OF THE INVENTION

The invention is directed to a device for loading a stent onto a balloon catheter and crimping the stent in place about the catheter in a surgical theater while avoiding any contact of the stent itself by the medical personnel. The invention eliminates the subjective factors presently involved in stent crimping and eliminates the need for tools such as pliers which might damage the stent during the crimping operation.

The device of the invention may also be disposable, eliminating the concerns associated with reusable devices including sterility and improper loading. It further serves as a device for safely encasing a stent by the manufacturer until the stent is conveniently inserted over and crimped onto the balloon catheter selected by medical personnel prior to delivery.

The hand held crimping device according to the invention has a longitudinal axis which generally defines the operational orientation of the device. Generally positioned along this axis are a stent holder, a catheter guide, a collet having radially compressible members which extend longitudinally for at least approximately the length of the stent to be placed and crimped, and a collet radial compressor which directs the radially compressible collet members in an inward radial direction in order to effect the desired stent crimping in response to hand applied digital forces imparted to the device by the person assembling the stent onto the catheter. Afterward, the catheter/stent assembly is easily removed from the crimping device leaving the stent only on the catheter so that the stent is ready for delivery into the patient by means of the catheter.

In a preferred embodiment, the device of the present invention includes an end unit or dome having an extension, preferably a nippled extension, a plurality of openings or slots for receiving fittings, tabs or inserts, and a base for receiving a chuck or collet; a collet having a base compatible with the collet receiving base of the end unit and a plurality of fingers which are radially compressible and which extend a longitudinal distance from said collet base; a main unit comprising a main body having a plurality of cammed fingers extending a distance on the distal side of the main body and capable of being inserted into the openings or slots of the end unit, an extension on the proximal side of the main body which extension has external cams suitable for receiving a cap, and a continuous opening through said cammed extension and main body; a cap having an opening therethrough, internal cams compatible with the external cams on the extension of the main body and an opening through said cap top; a compressible washer within said cap; a rotatable wheel or sleeve fitting about the cams of the main unit and a collet driver located within and at the proximal end of said sleeve; and a guide wire longitudinally extending from the center of said end unit through the proximal end of said cap.

The device of the invention optionally further includes a gauge by providing markings on the external surface of the device in order to facilitate accurate positioning of variable catheters within the device with respect to the stent being applied to the balloon of the catheter whether the catheter be a PTA or a PTCA catheter.

BRIEF DESCRIPTION OF THE DRAWINGS

FIG. 1 is a side elevational view of a preferred hand-held stent crimping device according to the invention depicting an end unit, sleeve, main unit and a cammed portion thereof, a cap and a guide wire.

FIG. 4 is a perspective view of the end unit illustrating a preferred arrangement for holding the stent and the distal portion of the catheter.

FIG. 9 is a perspective view of the end unit of this embodiment within which is embedded a guide wire and onto which a collet unit is fitted.

FIG. 10 is a perspective view of an illustrated embodiment of a main unit of the device, showing a main body, cammed fingers extending therefrom and finger tabs for insertion into slots of the end unit.

FIG. 11 is a perspective view which illustrates the main unit of FIG. 10 with the end unit and collet fitted thereto and held in place by positioning the main body finger tabs through the openings of this end unit.

FIG. 12 is a side elevational view of an ergonomically shaped embodiment of the invention illustrating a sleeve stop means, a gauge, retention of the stent within the device and continuous openings throughout the main body and cap.

DETAILED DESCRIPTION OF THE INVENTION

Figure 2:
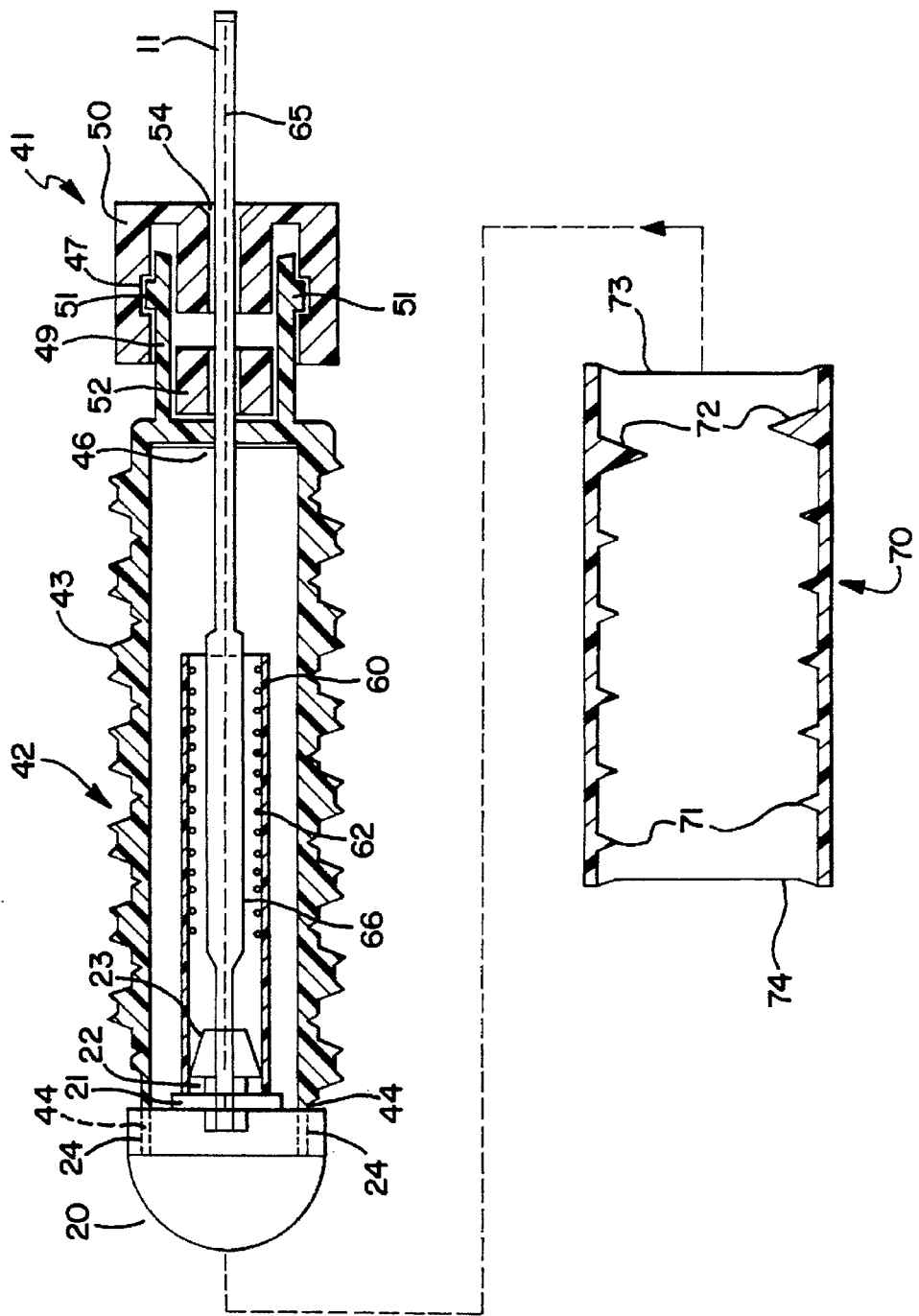
FIG. 2 is an exploded longitudinal generally cross-sectional view of the stent crimping device of FIG. 1 illustrating the positioning of a stent within the device by a holding member or means, a guide wire, an end unit, the main unit having a main body, cammed fingers and cammed extension, a cap with internal washer and a rotatable sleeve with a collet driver.

The device described herein utilizes a collet or chuck having a plurality of radially compressible members or fingers and a collet or collet finger radial compressor to radially compress a stent about a catheter. The compressor may move relative to the collet fingers and the device as a whole; for example, by rotation on a spiraled cam or by slidingly moving the compressor over the collet fingers. Alternatively, the collet may be slidingly moved through the compressor, for example, by pushing or pulling the collet through the compressor. In order to effect compression of the collet fingers and thereby crimp the stent within said fingers, the fingers or the compressor should be tapered on the side where the compressor and fingers make contact. In preferred embodiments, the collet fingers are tapered.

For example, in the embodiments shown herein utilizing a rotating sleeve or wheel, the collet fingers are tapered at both "ends" relative to the mid-section of said fingers. Where the compression is by slidingly moving the collet and fingers through the compressor, or the compressor over the fingers, it is preferred that the fingers be similarly tapered. In alternative embodiments, not illustrated, the collet fingers may have a ramp-up for the compressor to thereby increase the pressure on the collet fingers and crimp the stent, and a sharp drop-off thereafter to decrease the pressure on the collet fingers thus releasing the fingers and allowing the fingers to thereby return to their original, non-crimping position.

FIG. 1 illustrates an embodiment of the assembled device, generally designated as 10. This device has a longitudinal axis generally lying along an illustrated guide member 11. An end unit or assembly, generally designated as 20, conveniently supports various items as is more fully described herein. The illustrated main unit, generally designated as 40, functions as a body component by which the device can be easily grasped by the user. Also shown is a cap portion 50 which is useful in securing the catheter in place prior to crimping of a stent onto it. A moveable sleeve or ring, generally designated as 70, and is positioned for engaging a chuck or collet unit, generally designated as 80, in order to circumferentially and/or cylindrically radially compress a stent which is within the collet onto a catheter that had been inserted into the device.

Also visible in FIG. 1 is a main body 41 of the illustrated main unit and a portion of main unit cam or pathway 42. As more fully shown elsewhere herein, same can extend from the distal end of the main body. Illustrated securement in this regard includes terminal fittings, tabs or pegs which fit into openings, slots or receptacles in end unit 20 (see FIGS. 2, 3a, 3b, 9 and 11). Other securement arrangements are also contemplated. Cap portion 50 is in operational position on a threaded portion of the proximal end of main body 41 (see FIGS. 2, 3a and 3b), although other securing assembly approaches are possible. In this particular illustrated embodiment, the guide member is a guide wire 11 which is embedded in or otherwise secured to the end unit 20 and extends within device 10 to at least the proximal end of cap portion 50 and may optionally extend a distance beyond the proximal end of cap 50 as illustrated in FIG. 1.

Looking at device 10 as a whole, end unit 20 is at the distal end of the device, and cap 50 is at the proximal end of the device. When used with the components of the device of the invention, the terms proximal and distal will have the same relative meaning as with the device 10 as a whole.

The device 10 contains a stent 62 positioned within the device and held in place by a holding member, for example a length of tubing (see FIGS. 2, 3a, 3b and 4). While this holding member may be made of any suitable material, including various polymers, composites or metals, polymers are especially suitable, particularly shrinkable tubing such as, for example, shrinkable teflon tubing. The diameter and length of the stent 62 contained within the device may be marked on the device itself, the packaging containing the device or on both. For example, device 10 may have external markings, for example arrows 12, to indicate the position of the stent with respect to the device 10.

Catheters typically used with device 10 are balloon catheters having an open distal end. A typically catheter in this regard is designated 65, its balloon being shown at 66. Device 10 may or may not be specifically designed to be used with specific catheters. When so specifically designed, the open end of the catheter is simply slipped over guide wire 11 and inserted as far as possible into device 10. The balloon portion of the catheter will be automatically properly positioned within the stent, and the catheter can be held in place by tightening of cap 50 over the threaded or cammed portion of the proximal end of main body 41 to radially compress about said catheter a compressible washer 52 with said cap 50. The stent may then be crimped about the catheter as described herein.

Catheters which do not meet the specific parameters of the particular device 10 may nevertheless be used with the device. Using the optional external markings on device 10, for example arrows 12, the user determines how far the catheter must be inserted into device 10 in order for the balloon to be properly positioned within the stent and then inserts the catheter that distance. The catheter is held in place by then tightening cap 50 about the proximal end of main body 41 as mentioned above.

Figure 3A:
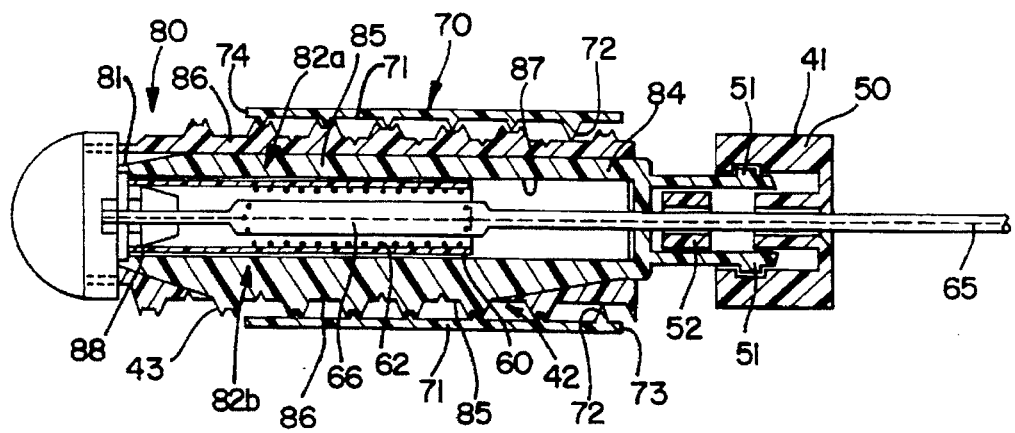
FIGS. 3a, 3b and 3c are modified cross-sectional views of the stent crimping device according to FIG. 2, these views also showing the collet or chuck assembly for crimping the stent by radial compression and differ with regard to the cam and cam follower design for the sleeve and main body finger-like extensions.
Figure 3B:
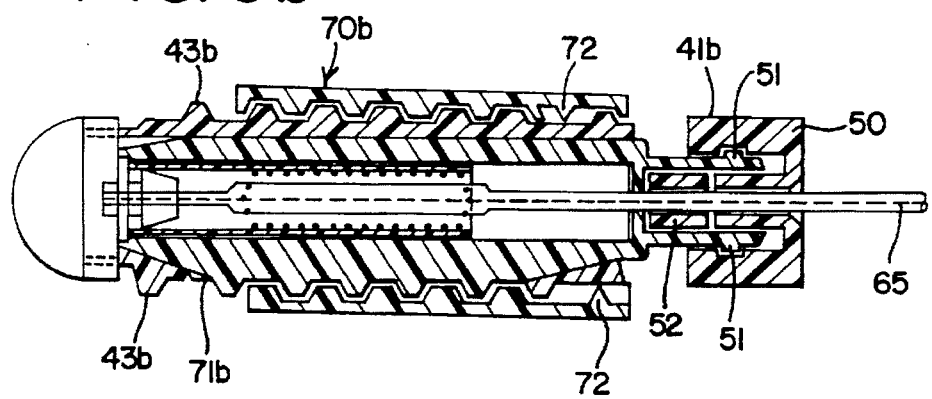

FIGS. 2, 3a and 3b are exploded longitudinal generally cross-sectional views of device 10. For clarity, the collet and collet finger elements of the invention which are depicted in FIGS. 3a and 3b have been omitted from FIG. 2, and the sleeve 70 is shown disassembled in FIG. 2.

FIG. 3a further illustrates elements of the exemplary device 10. An end unit or dome 20 has on its proximal side a collet base retaining member 21 of selected shape, an extension 22 with nippled end 23, a plurality of slots 24, with the guide wire 11 being embedded within end unit 20 and extending through extension 22 and nipple 23 for a distance from said end unit.

The chuck or collet unit 80 shown in FIG. 3a has a base 81 with an opening 89 (see FIG. 6) through said base, which opening is sized and shaped to fit about the selected shape of base retaining member 21 of end unit 20 and a plurality of fingers 82 extending a distance from the collet base 81. Fingers 82 are tapered on their outwardly radially extending sides such that they are thinner in radial cross-section near the collet base or distal portion 88, and near proximal end portion 84, than they are at collet finger mid-section 85. This thicker radial cross-section preferably continues for a length which is about the same as, and preferably longer than the length of the stent.

Main body represented generally by 41 has an externally threaded (or otherwise cammed) extension 49. Body or support 41 has the cam or pathway 42 and fittings or tabs 44, which fittings 44 fit into and/or connect with the openings or slots 24 of end unit 20, an opening through said main body 41 and extension 49 thereof, said opening extending from proximal end 45 to distal end 46. External threads 47 or the like are provided on extension 49. The cap 50 has internal threads 51 compatible with external threads 47 or the like, as well as an opening 54.

Cap 50 can function in the nature of a stasis valve. A compressible washer or fitting 52 is positioned within the cap 50, and wire 11 and a catheter may pass through this washer. Washer 52 is made of a material such that when cap 50 is tightened about cams 47 of main body extension 49, the washer is radially compressed about the catheter inserted over the guide to prevent longitudinal motion of the catheter with device 10 and thereby hold the catheter in place for crimping a stent contained within the device about the catheter inserted therein. Washer 52 may be made of silicone, latex or similar material.

Rotatable sleeve or wheel 70 is generally open from proximal end 73 to distal end 74, being generally lined with internal threads or cam followers 71 compatible with threads or cam surfaces 43 of main unit 40 and one or a plurality of collet drivers 72 for radially compressing the fingers 82 of collet 80 (see FIGS. 3a and 3b) to thereby effect crimping of the stent about the catheter. Cam or pathway 42 includes an indent 43 that follows the pathway 42. In the illustrated embodiment, both pathways 42 and indent 43 are generally spirally disposed, as seen in FIGS. 10 and 11. Cam followers 71 move through the indent 43 during operation of the device, as generally shown in FIG. 3. At the same time, the driver 72 engages the fingers 82, such as by following a path defined by groove 86. In fact, if desired, the driver 72 can also follow or etch a path 91 in the fingers 82 (shown in FIG. 6). For illustrative purposes, in FIG. 3a, the cross-section is taken such that the finger 82a is shown behind body 41, while the finger 82b is shown on top of body 41, this being shown by varying the section location on the various cylindrical components which are sectioned in FIG. 3a.

FIG. 3b illustrates an alternative for the rotatable sleeve and main body extensions shown in FIG. 3a. In FIG. 3a, body 41 has cam or pathway 42 having cammed surfaces 43; and sleeve 70 has internal threads or cam followers 71 compatible with cammed surfaces 43. As illustrated in FIG. 3b, a main body 41b has a cam or pathway 42b which comprises a rail-like cammed surface 43b and sleeve 70b has indent 71b which serve as the track for rail 43b. Sleeve 70b also has driver 72 as does sleeve 70. As in FIG. 3a, elements 43b and 71b are both spiral or helical in shape.

The collet driver 72 illustrated in the figures is generally spiral in shape over 360 degrees and has both a ramp-up and a ramp-down to facilitate movement on and off the main body pathway 42.

Figure 3C:
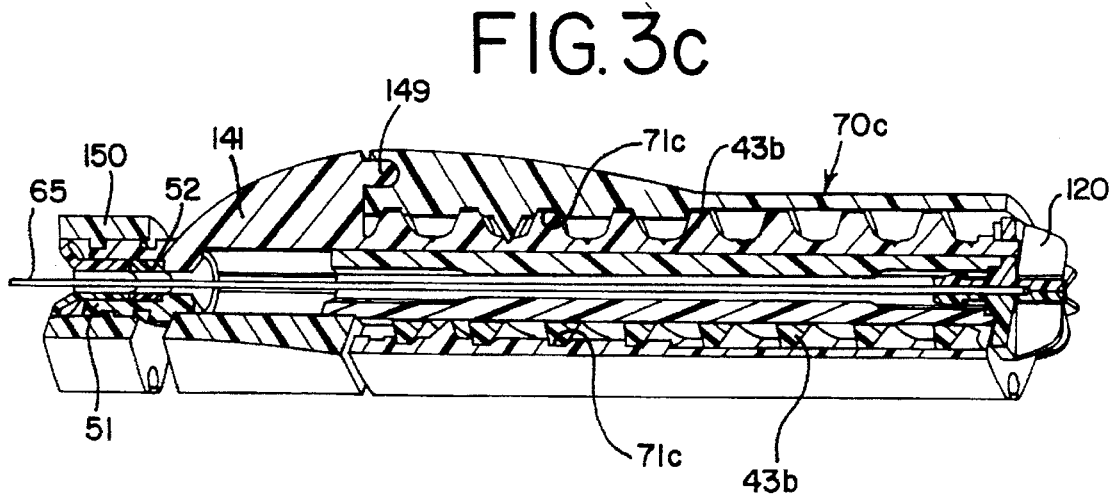

In FIG. 3a, sleeve 70 is illustrated as having cam followers 71 extending from approximately driver 72 to the distal end of the sleeve. In FIG. 3b, sleeve 70b is illustrated as having indents 71b extending from approximately the driver 72 to the distal end of the sleeve. In order to reduce the frictional forces encountered in rotating the sleeve about its pathway, an alternative embodiment as illustrated in FIG. 3c may be utilized. In this alternative embodiment, a sleeve 70c, is provided in which its indents 71c extend from approximately driver 72 to about the mid-point of sleeve 70c, or a short distance beyond its ramp-down location.

The thickness of the sleeve from the end of the ramp-down to the distal end of the sleeve is about the minimum thickness of the sleeve between sections of the cam follower from the proximal end to about the mid-point. In an alternative embodiment of sleeve 70b, indent 71b is continuous and circumferentially uniform from approximately the mid-point of sleeve 70b to the distal end thereof.

Also shown in FIGS. 2, 3a and 3b is a stent holding member or tube 60 having a distal end affixed about end unit extension 22 and nipple 23, which holding member 60 extends within device 10 in a proximal direction away from nipple 23. Stent 62 is shown held within the holding member 60.

Referring now to FIG. 4, a properly sized stent holding member 60 is positioned over end unit 20 extension 22, and nipple 23 until member distal end 64 abuts surface 25 of collet base retaining member 21. Preferably member 60 is shrinkable and it is then shrunk into place so it firmly engages the nipple 23. Stent 62 is positioned within shrinkable member 60 which assists in holding stent 62 into place. Alternatively, member 60 can be pre-shrunk about stent 62 and both inserted together before member 60 is shrunk about extension 22 and nipple 23. As a further alternative, member 60 and stent 62 can be properly position as described in herein, either sequentially or simultaneously, and the shrinking of member 60 about elements 22, 23 and 62 is carried out in a single step. It is preferable that shrinkable member 60 be of sufficient length to completely contain stent 62 in order to cushion the stent during the crimping procedure.

Stent holding member 60 is preferably made of a material which is not only shrinkable, but also has elastic properties after compression. After the stent has been crimped about the catheter, the stent holding member 60 is separated from the stent by its elastic properties which also aid in forcing the collet fingers back from their maximum compressive position. The stent crimped about the catheter can thus be readily removed from the crimping device free of the holding member.

FIG. 4 further illustrates the plurality of openings or slots 24 into which are fitted the tabs or fittings 44 of main unit 40 finger-like extensions 42. When snap-fit tabs or fittings, illustrated as 48 in FIG. 10, are used in practicing the invention, an end unit with flutes 26 on the distal side is preferred, and openings or slots 24 comprise an opening through base unit portion or flange 29 and between the flutes (see also FIGS. 9 and 11). If tabs or fittings 44 are to be held by friction, either of the illustrated shaped end tabs, or tabs or pins of other shapes, may be used in practicing the invention, the selection of such shapes being within the ability of those skilled in the art.

Figure 5:
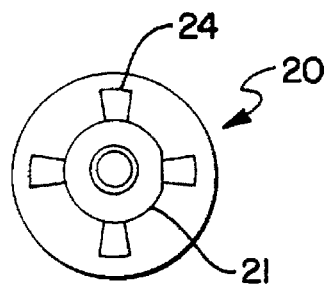
FIG. 5 is an end view of the proximal side of the end unit of this embodiment, illustrating a D-shaped ring for retaining the collet and openings or slots for receiving the main unit fingers.

FIG. 5 illustrates the proximal side of end unit 20 whereon retaining member 21 is generally "D" shaped. Pentagonal, hexagonal and other shapes familiar to those skilled in the art can also be used, the only criterion being that the collet base 81 cannot rotate about member 21.

Figure 6:
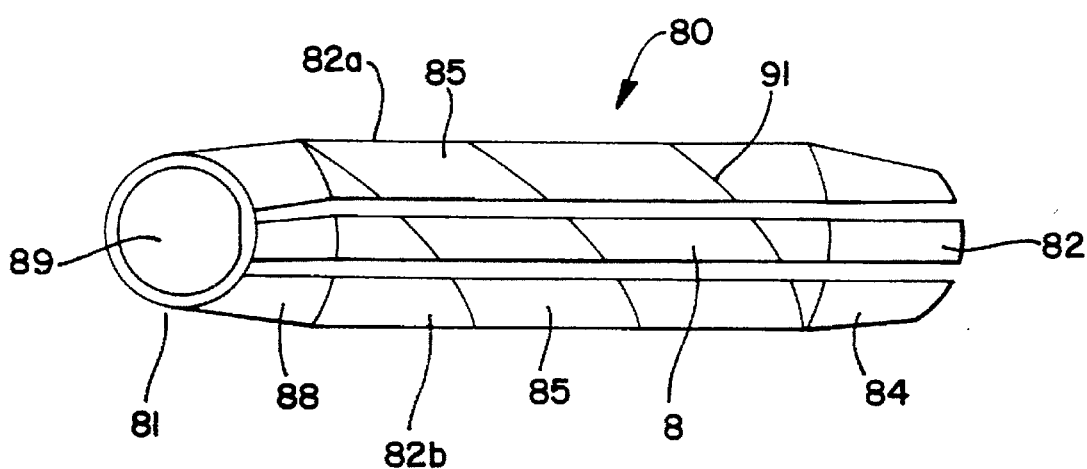
FIG. 6 is a side perspective view of the chuck or collet unit of this embodiment, illustrating the compressible fingers and a collet base having a D-shaped opening compatible with the D-shaped ring on the end unit.

Referring now to FIG. 6, once stent 62 and stent holding member 60 have been placed about extension 22 and nipple 23, a collet 80 is slipped over guide 11, and collet base 81 is positioned about retaining member 21 of 5 end unit 20. To insure the proper positioning of collet 80, base 81 has a shaped opening 89 compatible with the selected shape of retaining member 21. In FIG. 6, the opening 89 of collet base 81 has a general "D" shape so as to be "keyed" with respect to the similarly shaped retaining member 21. Numeral 91 illustrates the track which driver 72 will trace and etch on collet 80 as the driver traverses the device in a proximal to distal direction.

Figure 7:
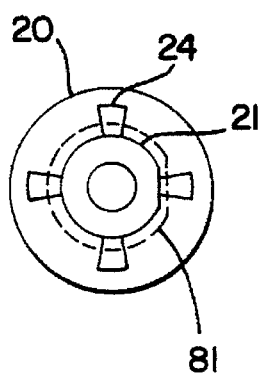
FIG. 7 is similar to FIG. 5 and further illustrates the fitting of the base of the collet about the D-shaped retaining ring of the end unit of this embodiment.

FIG. 7 is a top schematic view illustrating collet base 81 in place over end unit 20 retaining ring or member 21. The collet base may be held in place by frictional forces. Alternatively, collet base 81 and retaining member 21 may have a mutually congruent side opening to admit a retaining pin or screw (not illustrated). As is further illustrated in FIG. 7, end unit openings 24 extend radially outward beyond the circumference of collet base 81 when collet base 81 is in place about member 21.

Figure 8:
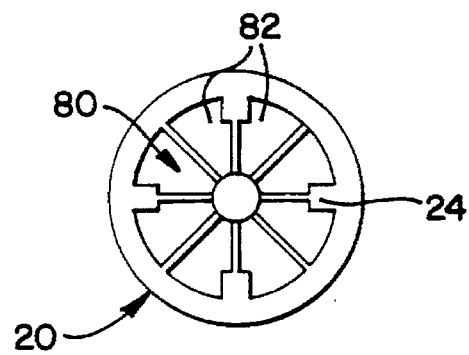
FIG. 8 is a view of the proximal end of the end unit with the collet base fitted thereto and further showing openings in the end unit of this embodiment.

FIG. 8 is a top view of an eight-fingered collet 80 in place over end unit retaining ring 21. The collet fingers 82 may be sized so that they do not interfere with openings 24 or, as is illustrated, each pair of fingers may have a cut-out section which, when taken together, constitute a notch whose position corresponds to that of one of the openings in base unit 20.

FIG. 9 illustrates a fluted base unit 20 with attached collet 80 and collet fingers 82 which have tapered ends represented generally by 84 and 88, the guide wire 11 passing longitudinally through the collet. The tapered collet finger ends generally represented by 84 and 88 (as shown in FIG. 9) are of lesser thickness than the mid-section of the collet which is generally represented by 85 so that the pressure exerted by collet driver 72 (see FIGS. 2, 3a and 3b) will be slowly and uniformly exerted on the stent and catheter with the collet when device 10 is used. As illustrated, the taper preferably is only on the radially outwardly directed side of the collet fingers so the inside surface defined by the fingers is generally cylindrical.

FIG. 10 illustrates main unit 40 with pathway 42 having cam surfaces 43. Tabs or fittings 44 are also shown. Main body 41 has an extension 49 with threads 47 for receiving cap 50 (see FIG. 2), and an opening through the main body 41 and extension 49 proximal end extending from proximal end 45 to distal end 46 of the main body. The cam surfaces 43 are spaced such that collet driver 72 of sleeve 70 (see FIG. 2 and 3) will travel along cam surfaces 43 when sleeve 70 is traversed along extension 42 in the distal direction in this illustrated embodiment when the device is in use. A snap-tab fitting is illustrated as 48 in FIG. 10.

FIG. 11 illustrates a main unit with end unit 20 and collet 80 fitted thereto. Also illustrated is a fitting in place and through one of the slots of end unit 20, this fitting being a snap fitting 48.

Generally, the device is assembled by placing the stent holding member 60 and stent 62 in position on base unit 20. Chuck or collet unit 80 is then fitted to the base unit. Sleeve 70 is placed about the finger-like extensions of main unit 40 with sleeve side 73 (see FIG. 2) adjacent and in proximity to main body 41. The collet/base unit combination is then inserted into the main body such that main body fittings or tabs 44 are inserted into openings 24 and guide wire 11 passes through the main body 41 and extension 49 opening from distal end 46 to proximal 45 and extends a distance beyond end 45. Washer 52 is placed within cap 50, the combination is slipped over guide wire 11, and cap 50 is positioned on cams 47. The device is then ready for use.

To use the device, a catheter is slipped over guide wire 11 and positioned with device 10. Wheel or sleeve 70 is then rotated about cam surfaces 43 such that the sleeve traverse the main unit in the direction from main body 41 to end unit 20, that is in the distal direction in the illustrated embodiment. As the sleeve 70 traverses the main unit, collet driver 72 within sleeve 70 first traverses the collet fingers 82 generally from proximal end 84 to mid-section 85, the thickness of the collet fingers increases and pressure is exerted on the collet fingers which drives them radially inwardly until collet finger inside surfaces 87 (see FIGS. 3a and 3b) encounter the stent and holder. Continued pressure on fingers 82 is exerted as the sleeve and driver further traverse the main unit causing the stent within the device to be crimped about the catheter. As the collet finger driver approaches end unit 20, for example, from mid-section 85 to collet base or distal section 88, the thickness of collet fingers 82 decreases due to tapering, and the fingers are released from their crimping position about the stent and catheter. Sleeve 70 can be rotated off the device. Cap 50 and washer 52 are removed from extension 49, and the catheter/stent combination is removed from the device ready for use.

FIG. 12 illustrates an alternative device 110 having an ergonomically shaped sleeve 170 with a stop bar 178. Also shown is main body 141 with stop bar 138 and stop 139 and cap or stasis valve 150. A catheter gauge 190 is recessed in the sleeve 170, main body 141 and stasis valve 150. Further illustrated is the position of the stent holding member 160 and stent 162 within the device, guide wire 111 which is embedded within the end unit and passes through end unit 120 extension 121, nipple 122, and stasis valve 150 and, extending, alternatively, either to the proximal end of valve 150 or outwardly a distance from said valve 150.

Figure 13:
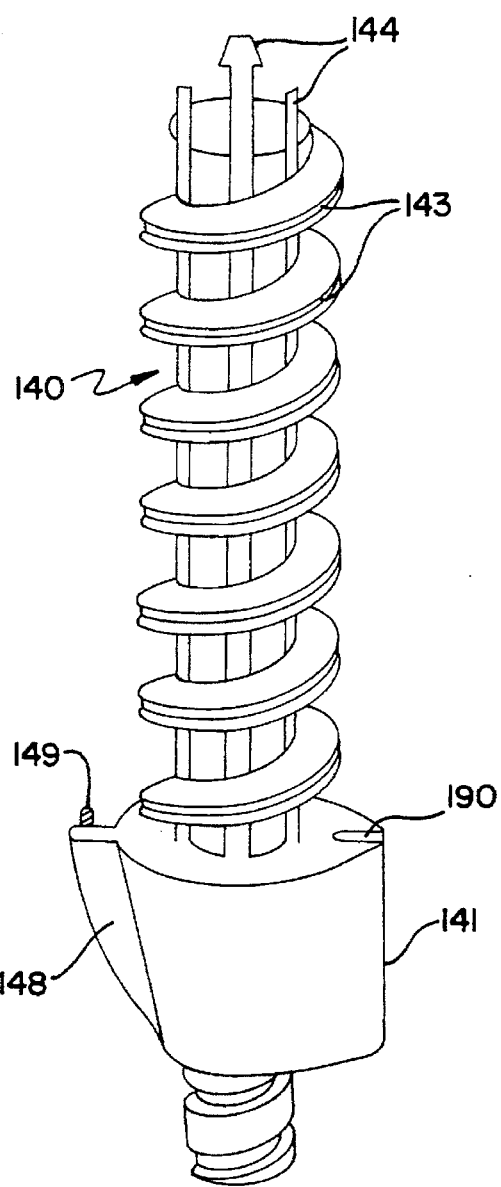
FIG. 13 is a perspective view of an embodiment of the main unit of the device of FIG. 12 illustrating cammed fingers extending therefrom, finger tabs for insertion into openings of the end unit and a portion of a sleeve stop, and a portion of the optional gauge.
Figure 14:
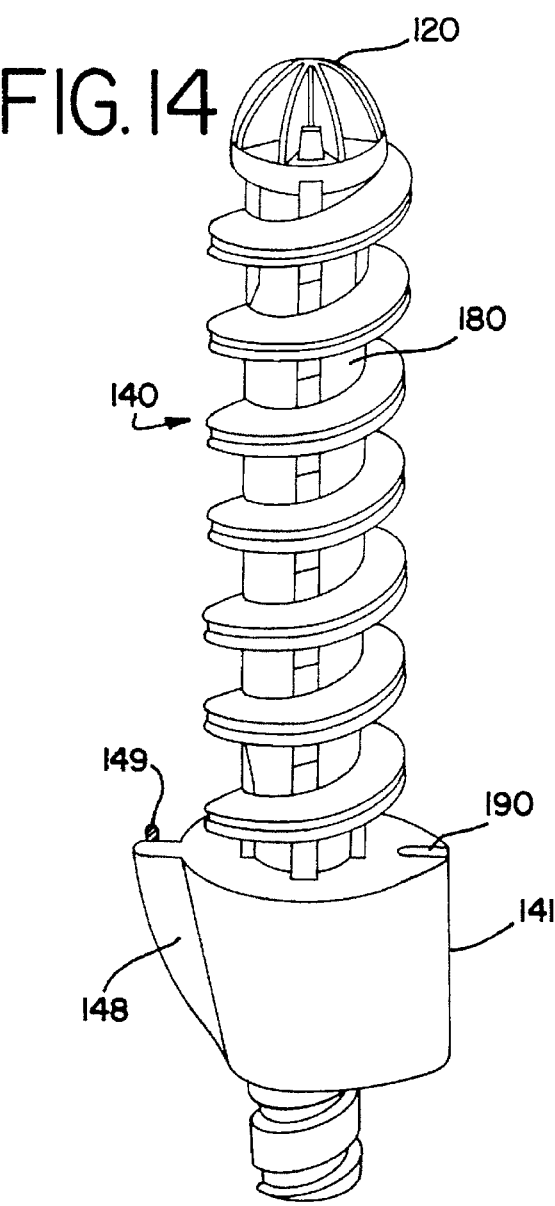
FIG. 14 illustrates the main unit of FIG. 13 with the end unit and collet fitted thereto and held in place by positioning the main body finger tabs through the openings of said end unit.

FIG. 13 illustrates the main unit 140 of the device of FIG. 12 and is similar to FIG. 10. It further illustrates stop bar 138, stop 139 and a section of catheter gauge 190 which is recessed and incorporated in central section 141. FIG. 14 illustrates main unit 140 with end unit 120 and collet 180 in place.

Figure 15:
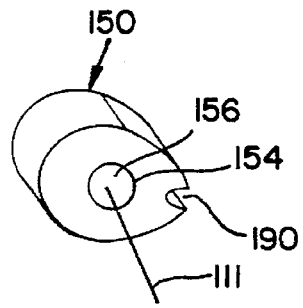
FIG. 15 is a perspective view of a side and the top of the cap of the FIG. 12 embodiment illustrating an opening in the top or proximal end of said cap, the washer positioned therein and the through which guide wire projects beyond the proximal end of the cap.
Figure 16:
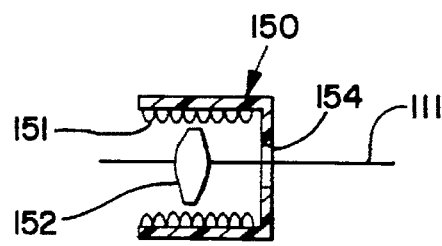
FIG. 16 is a cross-sectional side view illustrating the relationship between the cap, washer, internal cams and guide wire of the illustrated embodiments.

FIG. 15 illustrated stasis valve or cap 150 of this embodiment. Opening 156 extends through the opening 154 of the valve. A section of catheter gauge 190 and guide wire 111 pass through this opening 156 and extend a distance outwardly in a proximal direction. FIG. 16 is a cross-sectional view of cap or valve 150 illustrating opening 154, internal cams 151, and washer 152 positioned within said valve. Guide wire 111 passes through said washer, cap and cap opening and extending outwardly a distance from said cap.

The device 110 illustrated in FIGS. 12–16 is assembled and operated in approximately the same manner as the device illustrated in FIGS. 1–11. Stop bars 178 and 138 and stop 139 are added elements which allow sleeve 170 to be rotated in only one direction. Catheter gauge 190 is an added element to facilitate determining the depth to which a catheter must be inserted into the device. Markings 112 within the gauge indicate the position of the stent within the device.

It will be understood that the embodiments of the present invention which have been specifically described are merely illustrative of some of the applications of the principles of the present invention. Numerous modifications may be made by those skilled in the art without departing from the true spirit and scope of the invention.

I claim:

1. A stent crimping device for receiving a catheter and for placing and crimping a stent onto the catheter, the device comprising:

a guide member having a longitudinal axis generally coinciding with a longitudinal axis of the device;

a stent and a stent holding member positioned with respect to said guide member so as to accommodate a said stent slidingly inserted into said device along said guide member, into said device and into said stent;

a collet having radially moveable fingers, said fingers generally defining a cylinder lying along the longitudinal axis of the device;

a sleeve component which moves said fingers radially inwardly while said sleeve component is moved generally along the longitudinal axis of the device;

said fingers are positioned for engaging said stent holding member and for moving said stent holding member circumferentially inwardly upon movement of the sleeve component; and said stent holding member is positioned for moving said stent within the device circumferentially inwardly to crimp the stent onto a catheter.

2. The stent crimping device according to claim 1, wherein said sleeve component is rotatable generally about the longitudinal axis of the device.

3. The stent crimping device according to claim 2, wherein said sleeve component includes a driver which spirally engages said fingers to effect the movement of the fingers radially inwardly.

4. The stent crimping device of claim 3, wherein said sleeve driver is made of a material which is harder than the material from which the fingers are made so as to etch a grooved path in said fingers upon movement of said sleeve.

5. The stent crimping device according to claim 1, wherein said guide member is a guide wire located generally along the longitudinal axis of the device.

6. The stent crimping device of claim 5, wherein said stent is longitudinally held within said device about and spaced radially outwardly from said guide wire.

7. The stent crimping device according to claim 1, wherein said fingers each have a tapered proximal end portion and a tapered distal end portion.

8. The stent crimping device of claim 1, further including a main unit having a proximal extension and a cap releasably secured thereto, and an opening through said main unit, extension and cap through which said guide member extends, and a compressible washer is positioned within said cap over said guide member.

9. The stent crimping device of claim 1, wherein said sleeve component has external markings which, when said sleeve component is operationally fitted on said device, indicate the position of a stent within said device.

10. A stent crimping device comprising a stent holding member, a stent held within the stent holding member, a guide wire secured to the device and within said stent holding member and extending longitudinally through said stent and device, a collet having radially compressible fingers longitudinally extending in said device and about said stent and said guide wire, and a rotatable sleeve having a driver for compressing said collet fingers, said sleeve being about said fingers, said stent and said guide wire;

whereby when said sleeve is rotated about said collet fingers said driver radially compresses said fingers to crimp said stent by said stent holding member.

11. The device of claim 10, wherein said device contains a catheter therein, said catheter being longitudinally disposed about said guide wire and having an end section disposed between said guide wire and said stent.

12. The device of claim 10, wherein said sleeve driver is made of material harder than that of said collet finger material.

13. The device of claim 10, wherein said fingers each have a tapered proximal end portion and a tapered distal end portion.

14. The device of claim 10, further including a main unit having a proximal extension and a cap releasably secured thereto, and an opening through said main unit, said extension and said cap through which said member extends, and a compressible washer is positioned within said cap over said guide wire.

15. The device of claim 10, wherein said sleeve has external markings which, when said sleeve is operationally fitted on said device, indicate the position of said stent within said device.

16. A stent loading and crimping device for loading and crimping a stent about a catheter comprising:

(a) an end unit having a plurality of openings extending into said end unit from a proximal side thereof, a collet retaining base member on the proximal side thereof, an extension centered on said collet retaining base member, a stent retaining member fitted about said extension, a stent held by said stent retaining member and a guide wire centered and embedded within said end unit and extending longitudinally for a distance through said extension, said stent retaining member and said stent;

(b) a collet having a base with an opening therethrough and a plurality of radially compressible fingers extending outwardly from said base, said collet base opening being fitted about said end unit collet retaining member such that said fingers extend from said collet base toward a proximal end of the device;

(c) a main unit having a main body with a cam-like pathway extending generally along said main body and a proximal extension of said main body, an opening within said main body and proximal extension, and tabs at the distal end of said main unit which tabs fit into said openings of said end unit;

(d) a rotatable sleeve having internal cam followers and an internal driver, said sleeve fitting about said collet and cam-like pathway; and (e) a cap releasably positioned over said main body proximal extension, an opening through the proximal end of said cap, and a compressible washer within said cap.

17. The device of claim 16, wherein said collet finger members are radially thickest at a center section of said fingers.

18. The device of claim 16, wherein said sleeve driver is made of material harder than that of said collet fingers.

19. The device of claim 16, wherein said sleeve has external markings which, when said sleeve is operationally fitted on said device, indicate the position of a stent within said device.

* * * * *